(12) United States Patent
Matsuzaki (10) Patent No.: US 11,147,703 B2
(45) Date of Patent: *Oct. 19, 2021

(54) MECHANICAL ASSISTED ACTIVE ORTHOSIS USING A ROBOTIC APPLICATION

(71) Applicant: Tokio Matsuzaki, Tokyo (JP)

(72) Inventor: Tokio Matsuzaki, Tokyo (JP)

( * ) Notice: Subject to any disclaimer, the term of this patent is extended or adjusted under 35 U.S.C. 154(b) by 169 days.

This patent is subject to a terminal disclaimer.

(21) Appl. No.: 16/507,024

(22) Filed: Jul. 9, 2019

(65) Prior Publication Data

US 2019/0328568 A1 Oct. 31, 2019

Related U.S. Application Data

(63) Continuation of application No. 15/420,085, filed on Jan. 30, 2017, now Pat. No. 10,342,691.

(60) Provisional application No. 62/289,232, filed on Jan. 30, 2016.

(51) Int. Cl.
| | |
|---|---|
| *A61F 5/01* | (2006.01) |
| *A61B 5/0476* | (2006.01) |
| *A61B 5/0488* | (2006.01) |
| *A61B 5/11* | (2006.01) |
| *A61B 5/00* | (2006.01) |
| *A61B 5/369* | (2021.01) |
| *A61B 5/389* | (2021.01) |

(52) U.S. Cl.
CPC ............ *A61F 5/0125* (2013.01); *A61B 5/112* (2013.01); *A61B 5/1121* (2013.01); *A61B 5/369* (2021.01); *A61B 5/389* (2021.01); *A61B 5/7282* (2013.01); *A61B 2562/0219* (2013.01)

(58) Field of Classification Search
CPC .... A61F 5/0123; A61F 5/0125; A61F 5/0476; A61F 5/0488; A61F 5/122; A61F 5/1121; A61F 5/7282; A61F 2562/0219; G05B 2219/40305

See application file for complete search history.

(56) References Cited

U.S. PATENT DOCUMENTS

| | | |
|---|---|---|
| 8,057,414 B2 | 11/2011 | Nace |
| 2013/0190669 A1 | 7/2013 | Rokosz et al. |
| 2015/0005686 A1 | 1/2015 | Kazerounian et al. |
| 2017/0042467 A1* | 2/2017 | Herr ..................... A61B 5/7271 |

FOREIGN PATENT DOCUMENTS

WO 2011030641 A1 3/2011

* cited by examiner

*Primary Examiner* — Daniel J Colilla (57) ABSTRACT

A knee orthosis provides varying levels of support to a patient during a stance phase and a swing phase of a gait cycle. The orthosis comprises an upper auxiliary support, a lower auxiliary support, an actuator, a sensor configured to detect a plurality of leg movements during the gait cycle and to output a plurality of detection signals corresponding to the detected leg movements, and a processor configured to determine whether the knee is in the stance phase or the swing phase of the gait cycle, to control the actuator to apply pressure on the lower auxiliary support when the knee is in the stance phase, and to release pressure when the knee is in the swing phase.

20 Claims, 6 Drawing Sheets

MECHANICAL ASSISTED ACTIVE ORTHOSIS USING A ROBOTIC APPLICATION

RELATED APPLICATIONS

This application is a continuation of U.S. patent application Ser. No. 15/420,085, filed Jan. 30, 2017, which claims priority to U.S. Provisional Application No. 62/289,232, filed Jan. 30, 2016, each of which is hereby incorporated by reference in its entirety.

TECHNICAL FIELD

The disclosed embodiments relate generally to orthosis devices, and in particular to a mechanical assisted active orthosis using a robotic application.

BACKGROUND

Osteoarthritis (OA) is the most common degenerative disease of the human articular cartilage. OA causes pain and deformity of the articular joint, leading to significant functional deficiencies in daily life. OA occurs in the weight-bearing joints of the hips, spine, and most commonly, the knees. Many adults with OA have arthritis-attributable activity limitations, and they have a significantly worse quality of life than those without arthritis. Medical cost is another OA-related issue. The number of adults with arthritis continues to rise, resulting in growing numbers of total knee arthroplasty (TKA) procedures. Due to the increasing burden of treatment for OA, there is a need for low cost, high impact treatment alternatives.

In western countries, OA symptoms are more prevalent in the medial compartment of the knee than in the lateral compartment. The external knee adduction moment (KAM) has been developed for understanding the mechanical etiology of medial compartment knee OA. In the stance phase, the first peak of the KAM occurs during early stance, while the second peak occurs during late stance. The KAM is considered a surrogate measure for the medial tibiofemoral contact force and is widely used to quantify the load reducing effect of therapeutic intervention from devices such as wedged insoles and knee braces. In vivo analyses with instrumented knee prostheses have revealed a strong correlation between medial compartment loading and the KAM. The first peak of the KAM during walking has been linked with the presence of pain and severity of medial compartment knee OA. Reducing this peak can alleviate the pain while preventing further development of OA. Therefore, there is a need for devices that can reduce the first peak of the KAM as a therapeutic target.

The standard treatments for symptomatic knee OA are pharmacological treatments including nonsteroidal anti-inflammatory drugs (NSAIDs) or Tramadol, rehabilitation for cases of mild OA, orthoses, and partial or total knee replacement for severe OA. Other options include injection-based biomaterials, disease-modifying OA drugs, and regenerative therapy, but these options can be challenging. Despite the fact that OA patients are mostly over sixty years old, the healing potential linked to regenerative therapy decreases for patients older than sixty. The most effective method for treating OA in elderly people is TKA, which corrects the bone alignment in order to modify the mechanical loading and kinematics in the knee. Although most patients are relieved of pain, some feel dissatisfied with TKA. There is no strong evidence for the effectiveness of treatment between NSAIDs/rehabilitation and TKA in the mild OA population. Rehabilitation can be an effective therapeutic approach, but regarding the mechanism, the benefits of physical therapy may not be correlated with the reduction of the KAM, which indicates that rehabilitation may be inadequate to slow OA development.

On the other hand, orthotic knee braces have been developed and designed for reducing the load on the knee, and can be effective in reducing pain. However, braces can be inadequate for reducing the load while standing, or reducing biomechanical alterations while walking. Further, after continual use, muscle weakness can begin to occur. Therefore, there is a need for an orthosis that can reduce the loading of the knee without damaging the muscle surrounding the knee, not only during passive use (i.e. sitting), but also during active use (i.e. standing and walking).

Comparison with Related Art

U.S. Pat. No. 8,057,414 discloses an off-loading brace which is used in a clinical setting. This brace is designed to reduce the loading on either the medial or lateral side of the tibiofemoral joint. The effect of this brace is limited, as it is inadequate to reduce the load in standing and biomechanical alteration in walking. Further, after continual use, muscle weakening begins to occur since the brace has a force strap which tightens the extensor muscle and leads to immobilization of the knee.

Similarly, Int'l Pub. No. WO 2011030641 discloses a brace which intermittently controls expansion and contraction of an actuator unit. However, this brace also tightens the muscle, and does not achieve adequate reduction of knee loading during walking. This brace also has force straps on the thigh and the calf, which tightens the extensor muscle and leads to immobilization of the knee. In addition, this brace may reduce vascular disturbance, but does not reduce force on the knee joint.

As a further example, U.S. Pub. No. 20150005686 discloses a passive knee brace. This brace may reduce loading of the knee due to actuation of a spring and damper. Since this is not an active orthosis, however, the force generated from the spring and damper can vary due to their passive nature.

Lastly, U.S. Pub. No. 20130190669 discloses an approach which provides a geared motor to support the thigh. However, this device does not reduce knee loading and there is a risk that the muscle supported by the powered gear will be weakened during long term use.

SUMMARY

An active, adaptive, and dynamic orthosis is an innovative therapeutic improvement over traditional orthoses and could slow or prevent OA development by reducing knee adduction moment or loading of the knee without damaging muscle surrounding the knee.

In accordance with a first aspect of the robot-assisted orthosis, the orthosis includes a waist belt and an auxiliary part extending from the waist belt to a calf region with a freely bending hinge. A battery pack or other mobile power supply can be coupled to the waist belt or any other part of the orthosis.

In accordance with a second aspect of the robot-assisted orthosis, the orthosis includes an actuator, a processor, and a sensor. Detected data from the sensor can include acceleration, force, angulation, electromyography (EMG), electroencephalography (EEG), or any combination thereof. The processor analyzes the data to determine which phase of the gait cycle the leg is in, and activates or deactivates the actuator accordingly.

In accordance with a third aspect of the robot-assisted orthosis, the user can specify customized movement levels and activation windows. Further, the user can train the orthosis by operating the processor in a training mode, and can set different modes of operation based on different physical activities.

DETAILED DESCRIPTION OF EMBODIMENTS

Figure 1:
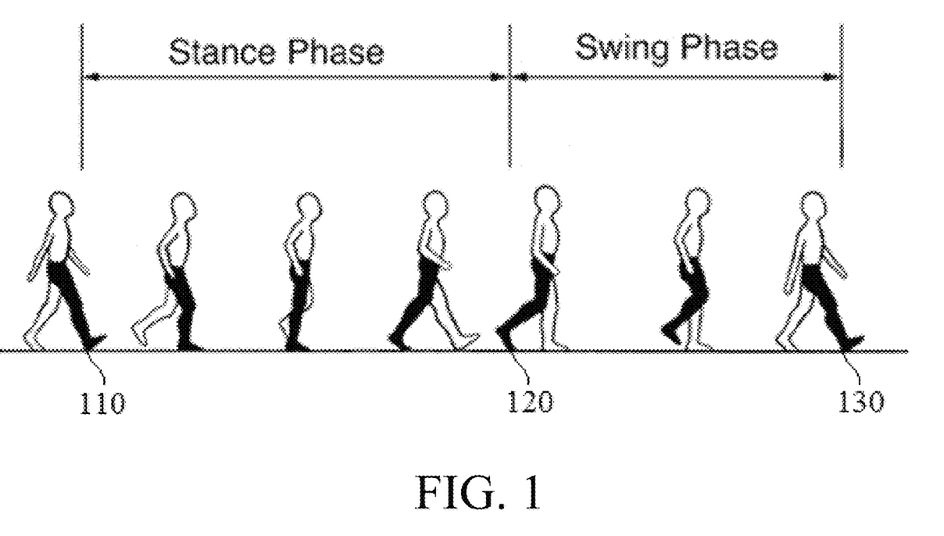
FIG. 1 depicts a gait phase diagram of a walking person, in accordance with manipulations of the KAM in some embodiments.

FIG. 1 depicts a gait phase diagram of a walking person. Stance phase lasts from heel strike 110 to toe off 120, and accounts for 60% of a single gait cycle. During the stance phase, the foot is on the ground and the body passes over its top, loading the knee. The rest of the gait cycle, swing phase, lasts from toe off 120 until the next heel strike 130.

Figure 2:
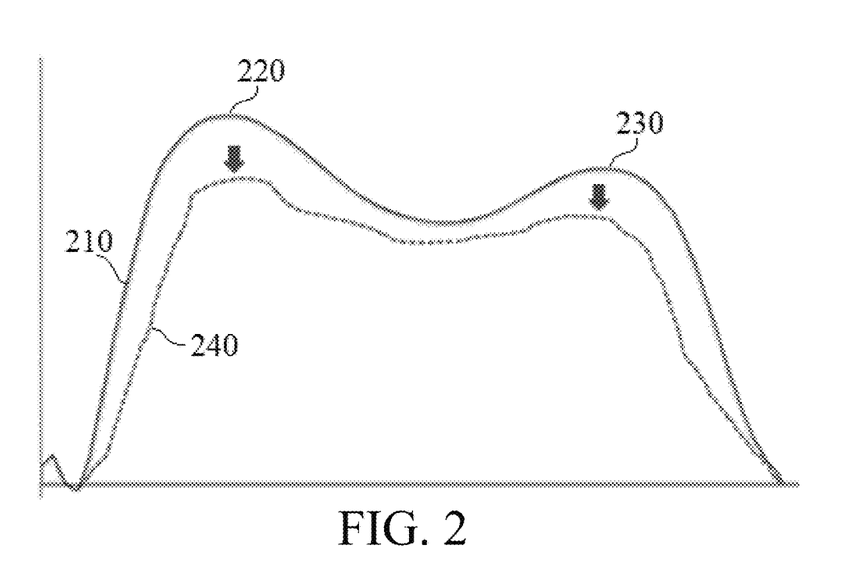
FIG. 2 depicts a graph of the KAM before and after being modified in accordance with some embodiments.

FIG. 2 depicts a graph of the KAM during the stance phase. Graph 210 is a normal KAM, and includes two peaks, 220 and 230, which represent the two time periods during stance phase with the most pressure, and consequently, the most knee loading. A goal of the disclosed embodiments is to alleviate loading in the knee, resulting in a reduced KAM 240.

Figure 3:
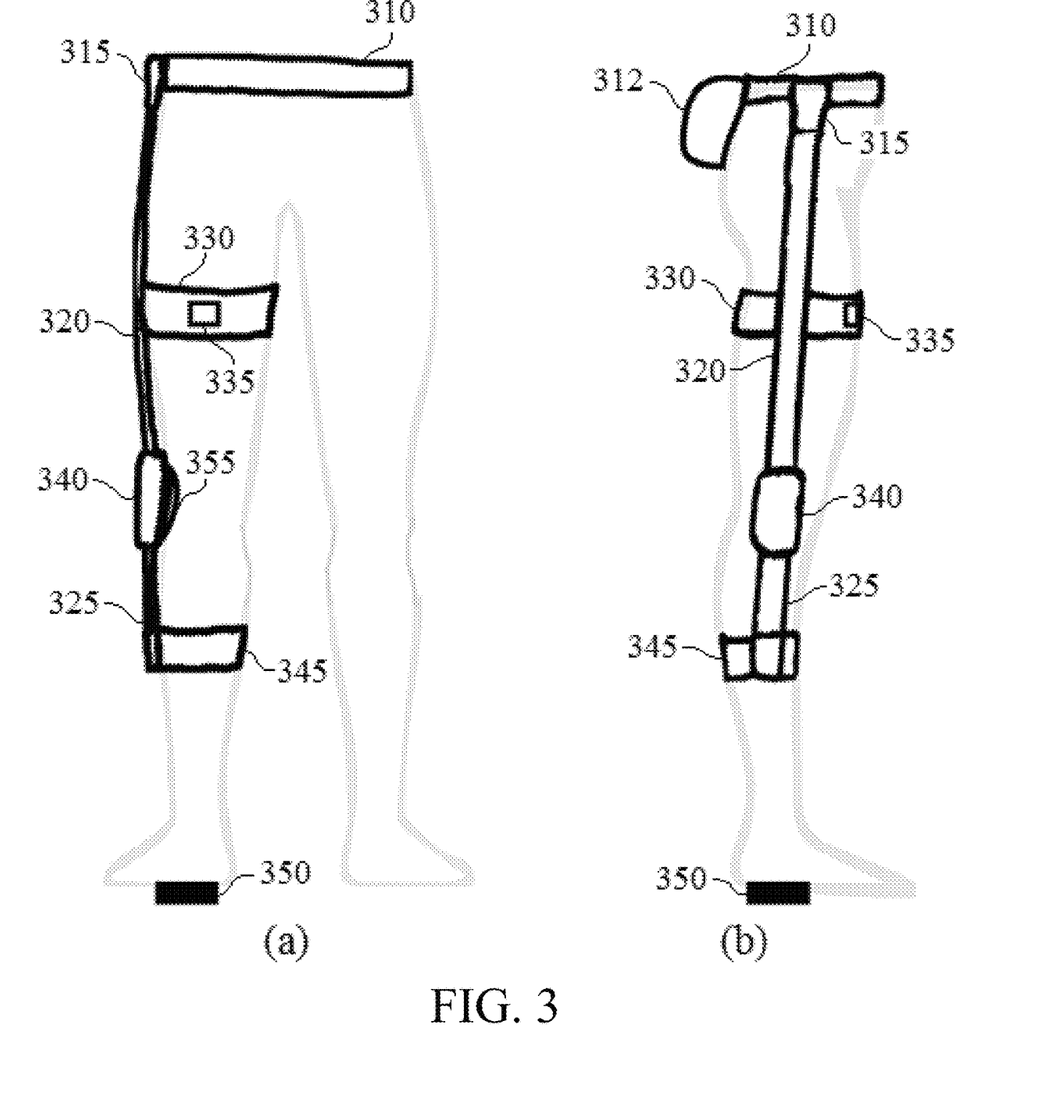
FIG. 3 depicts a frontal view and a lateral view of a robot-assisted orthosis in accordance with some embodiments.

FIG. 3 depicts frontal (a) and lateral (b) views of a robot-assisted orthosis. Waist belt 310 and an auxiliary part comprising a waist region 315, a thigh region 320, and a calf region 325, along with thigh strap 330 and calf strap 345, work together to actuator unit 340 which comprises an actuator and a freely bending hinge. Movement sensor 335 is coupled to thigh strap 330, and an optional force sensor 350 is placed underneath the user's foot.

Waist belt 310 can comprise rubber, leather, nylon, or any other flexible material or combination thereof. Auxiliary parts 315-325 can comprise carbon fiber, metal including stainless steel or titanium, or any other rigid material or combination thereof. Auxiliary part 315 and waist belt 310 can be connected by a metal connector, or any other kind of connector that can affix a flexible belt to a rigid material. It is appreciated that placement of waist belt 310 will depend on the user's unique body shape, and can be adjusted to account for comfort and stability. For instance, if waist belt 310 is more comfortable being placed higher or lower than depicted in FIG. 3, then it can be adjusted accordingly as long as the belt still provides adequate stability to support the rest of the orthosis.

Thigh strap 330 and calf strap 345 can support the corresponding auxiliary parts by physically coupling the auxiliary parts to the leg. It is appreciated that placement of the straps will depend on the user's unique leg shape, and can be adjusted to account for comfort and stability. For instance, if thigh strap 330 is more comfortable being placed closer to the knee or closer to the waist, then it can be adjusted to strap around those regions as long as the strap still provides adequate stability for auxiliary part 320. Similarly, if calf strap 345 is more comfortable being placed closer to the knee or closer to the ankle, then it can be adjusted to strap around those regions as long as the strap still provides adequate stability for auxiliary part 325. As used herein, the terms "thigh region" and "calf region" shall be defined as any region between the knee and waist, and the knee and ankle, respectively, in which placement of a strap can provide stability for corresponding auxiliary parts 320 and 325.

A portable power source such as a battery pack, a processor such as a microcontroller, and a memory can be coupled to the back side of waist belt 310 in a housing 312. Alternatively, the power source, processor, and memory can be placed on any portion of waist belt 310 or any other part of the orthosis that does not impede the user's freedom of movement. Optionally, a computing device (not shown) such as a smartphone, a laptop, or a desktop computer can be communicatively coupled to the processor. Alternatively, the on-board processor can execute all of the functions disclosed herein, without the need for a separate computing device. Power and communication cables from the battery and processor, respectively, can follow a path along auxiliary part 320 to actuator 340. Alternatively, the processor may communicate wirelessly with actuator 340, in order to decrease the amount of wiring running from the waist to the knee. In the case of wireless communication, the processor may be communicatively coupled with a transmitter, the actuator may be communicatively coupled with a receiver. As an alternative of, or in addition to, the actuator, some embodiments can include a relay module to control forward and backward motion of a motor.

Sensor 335 is communicatively coupled to actuator 340, and an optional force sensor 350 can be placed underneath the user's foot. These sensors can be communicatively coupled with a wireless transmitter, and the resulting wireless signals can be transmitted to the onboard processor in housing 312, an external computing device, or both. A power cable can descend from auxiliary part 320 to force sensor 350, or a power supply can be mechanically coupled to force sensor 350. Sensor 335 can be mechanically coupled to thigh strap 330, auxiliary part 320, calf strap 345, auxiliary part 325, actuator 340, or any other part of the user's leg, as long as readings from the sensor can be used to determine where the user's leg is in the gait cycle. Sensor 335 can be an acceleration sensor, an angulation sensor, an EMG/EEG sensor, or any combination thereof. The sensor can be any sensing device that is configured to detect the user's leg motion during the gait cycle as depicted in FIG. 1.

Pad 355 can be placed between actuator 340 and the knee, and can serve as a cushion for comfort and stability. Since the orthosis is not strapped to the immediate area of the knee, pad 355 can provide further stability to the knee region (defined as the region between the thigh region and the calf region).

Figure 4:
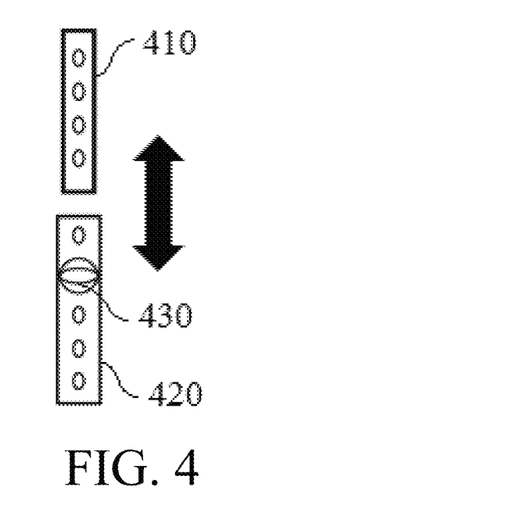
FIG. 4 depicts an adjustable mechanism for an auxiliary part in accordance with some embodiments.

FIG. 4 depicts a nonlimiting example of an adjusting mechanism for auxiliary parts 320 and 325. Since every leg has unique dimensions, auxiliary parts 320 and 325 can be adjusted in order to provide optimal comfort and stability. An adjustment mechanism can comprise two parts 410 and 420, which represent two segments of a single auxiliary part. Parts 410 and 420 can include evenly spaced holes through which a fastener 430 can be installed. Depending on how many holes overlap when installing fastener 430, the length of the auxiliary part can be adjusted accordingly. It is appreciated that in place of the specific example in FIG. 4, any other adjusting mechanism can be used, as long as the length of each auxiliary part 320 and 325 can be increased or decreased for optimal fit. Alternatively, auxiliary parts 320 and 325 may be of fixed length, with the user having a choice of prefabricated lengths, or the user having the option to trim a portion of each auxiliary part in order to achieve optimal fit.

Figure 5:
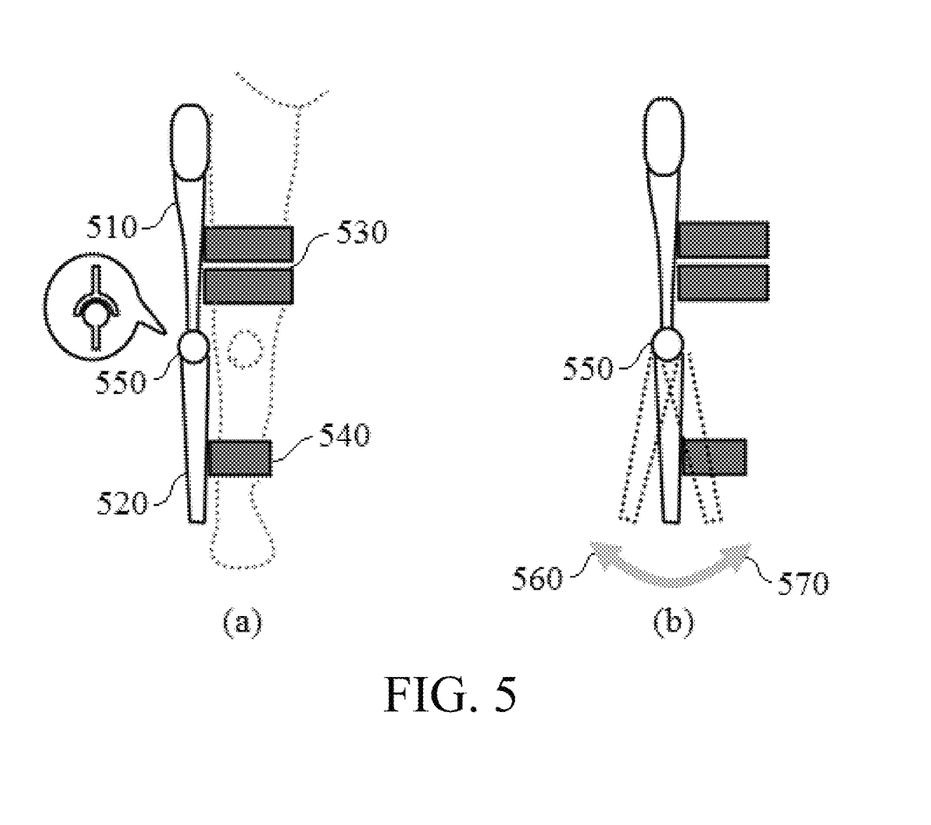
FIG. 5 depicts frontal views, with and without a leg, of a robot-assisted orthosis in accordance with some embodiments.

FIG. 5 depicts a frontal view (a) of an orthosis mounted to a leg, and a frontal view (b) of the same orthosis without the leg in order to better display various movements in accordance with some embodiments. Auxiliary parts 510 and 520, together with straps 530 and 540, stabilize actuator 550. A nonlimiting example of actuator 550 comprises a ball joint. In this configuration, auxiliary part 520 can move in a valgus direction 560 (away from the center of the body) or a varus direction 570 (toward the center of the body). When moved in a valgus direction, auxiliary part 520 puts an outward pressure on the calf region of the leg (direction 560), reducing pressure on the medial compartment of the knee. Conversely, when moved in a varus direction, auxiliary part 520 puts an inward pressure on the calf region of the leg (direction 570), reducing pressure on the lateral compartment of the knee.

Figure 6:
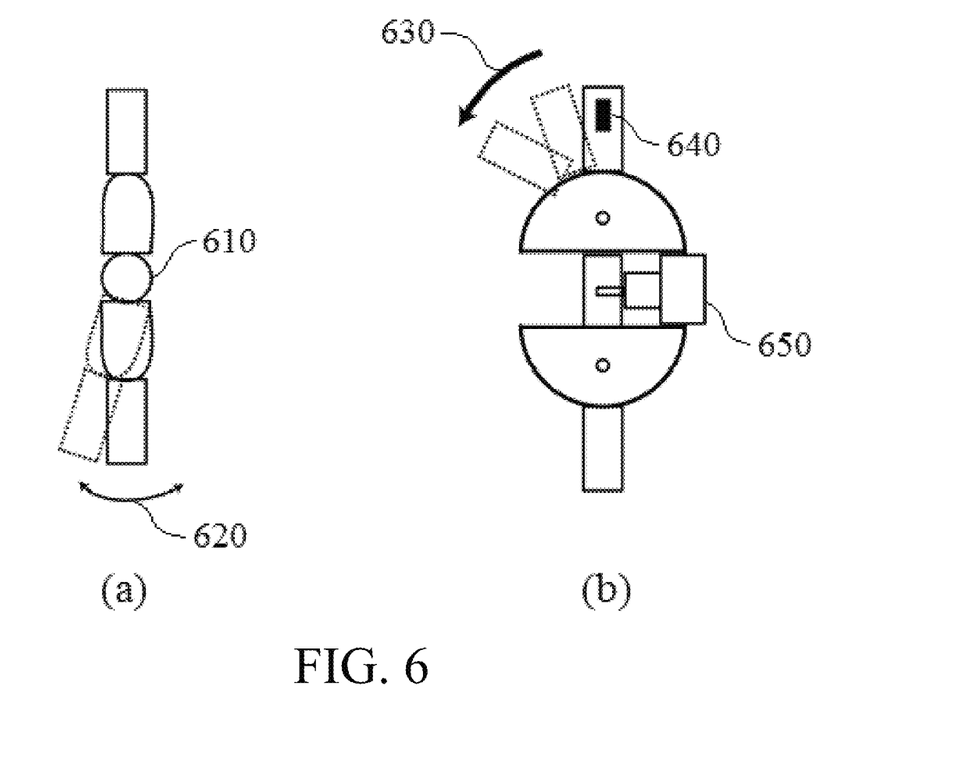
FIG. 6 depicts a frontal view and a lateral view of an actuator and surrounding parts in accordance with some embodiments.

FIG. 6 depicts a frontal view (a) and a lateral view (b) of the actuator portion in accordance with some embodiments. Actuator 610 moves the lower part of the orthosis in a valgus or varus direction 620. As the user walks, the upper part of the orthosis moves along with the user's thigh in a direction of flexion 630. Sensor 640 (corresponding with sensor 335 in FIG. 3) detects this movement, and causes motor 650 to actuate the lower part of the orthosis in direction 620 during the stance phase.

More specifically, and with reference to FIGS. 1, 3, and 5, when the user's leg begins a new gait cycle, one sensor or a combination of sensors 335 and 350 detects a heel strike at position 110. Upon detection of the heel strike, the processor activates actuator 340, which moves part 325 from a neutral position to a valgus or varus position, as depicted by directions 560 and 570. When the sensor or combination of sensors detects toe off at position 120, the processor deactivates actuator 340, which moves part 325 back to a neutral position, as depicted by part 520. Actuator 340 remains deactivated, and part 325 remains in the neutral position for the duration of the swing phase, until the sensor or combination of sensors detects the next heel strike at position 130, and the cycle repeats.

In some embodiments, the heel strike detection can be made by at least one of a combination of sensors, including an accelerometer, an angular sensor, and a force sensor.

An accelerometer can measure rates of change in velocity of the leg. The leg moves with a relatively constant velocity during the stance phase. At the beginning of the swing phase, the leg's velocity rapidly increases as the leg swings ahead of the opposite leg in preparation for the next heel strike, and then rapidly decreases at the end of the swing phase. Therefore, the beginning of a stance phase can correspond with a negative acceleration, and the end of the stance phase can correspond with a positive acceleration.

An angular sensor can measure relative positions and orientations of the leg. As the leg moves through the gait cycle, the angular sensor can calculate orientations with respect to a specified reference position as expressed by the amount of rotation necessary to change from one orientation to another about a specified axis. Therefore, the beginning and end of the stance phase can correspond with predetermined angular orientations.

A force sensor can measure relative changes or rates of change in force caused by the foot coming in contact with the ground. As the leg moves through the gait cycle, the foot hits the ground at the beginning of the stance phase, and does not leave the ground until the end of the stance phase. Specifically, a positive change of force will last from the heel strike through the midpoint of the stance phase, and a negative change of force will last from the midpoint of the stance phase through the end of the stance phase. On the other hand, the most positive rate of change of force will be at the instant of heel strike at position 110, and the most negative rate of change of force will be at the instant of toe off at position 120. Therefore, the beginning of the stance phase can correspond with a positive change or rate of change in force, and the end of the stance phase can correspond with a negative change or rate of change in force.

In some embodiments, the user can set the valgus/varus angle using the external computing device. For example, the user can set the angle on a scale of one to ten, with one being the smallest possible angle (corresponding with the least amount of pressure on the leg), and ten being the largest possible angle (corresponding with the highest amount of pressure on the leg). It is appreciated that other scales and methods for changing the valgus/varus angle are conceivable, including manual adjustment. By allowing the user to set the valgus/varus angle, the user can find the optimal level of comfort and stability.

In some embodiments, the user can also set the activation window of the actuator. For example, the user can set an activation window on a scale of one to ten, with one being the shortest possible window (corresponding with the actuator being deactivated for most, if not all, of the gait cycle), and ten being the longest possible window (corresponding with the actuator being activated for most, if not all, of the gait cycle). However, no matter the setting, it is preferred that the actuator be deactivated at least during the swing phase in order to prevent muscle weakness. It is appreciated that other scales and methods for changing the activation window of the actuator are conceivable, including manual adjustment in order to keep the brace from exerting pressure during the swing phase. By allowing the user to set the activation window of the actuator, the user can find the optimal level of comfort and muscle weakness prevention. For instance, while a longer activation window may be more comfortable, a short activation window will be more effective in preventing muscle weakness.

In some embodiments, the user can train the orthosis by setting the computing device to a training mode, during which the computing device analyzes any of acceleration, angle, orientation, and force during a predetermined number of gait cycles. By recording the aforementioned characteristics over a number of gait cycles, the processor can determine maximum and minimum values corresponding with each characteristic, and set thresholds accordingly.

For example, during a training mode, the processor can record a plurality of acceleration levels over time, determine a maximum acceleration, and determine a minimum acceleration. The processor can subsequently set a threshold such that acceleration levels below the threshold signify a beginning of a stance phase, and acceleration levels above the threshold signify an end of the stance phase.

As a further training example, the processor can record a plurality of angle and orientation data, determine a maximum angle or orientation, and determine a minimum angle or orientation. The processor can subsequently set a threshold such that angles or orientations higher than the threshold signify a stance phase, and angles or orientations lower than the threshold signify a swing phase, or vice versa, depending on the reference position or the reference axis.

As a further training example, the processor can record a plurality of force levels over time, determine a maximum force level, a minimum force level, a maximum rate of change of force levels, and a minimum rate of change of force levels. The processor can subsequently set a threshold such that force levels below the threshold signify a swing phase, and force levels above the threshold signify a stance phase. In addition, or in the alternative, the processor can set a threshold such that rates of change above the threshold signify a first portion of a stance phase, and rates of change below the threshold signify a second portion of the stance phase.

In the above training examples, the processor can determine maximum and minimum values by recording peaks and troughs in the sensor data, and calculating an average peak and an average trough over time. The amount of time over which sensor readings are recorded can be predetermined (i.e. over N gait cycles, where N is an integer). Alternatively, the amount of time over which sensor readings are recorded can be adaptively set accordingly to a standard deviation of peak and trough values. For example, once the peak and trough values fall below a predetermined threshold of standard deviation, the processor can assume that it has recorded a relatively accurate snapshot of the user's gait such that further recordings will not cause any significant changes to the maximum and minimum values.

In some embodiments, the user can set a plurality of profiles for the orthosis, depending on the user's activity. For example, when the user is running, climbing stairs, or standing still, the user may require different valgus/varus forces, depending on the unique characteristics of the user's movement, as well as the physical characteristics of the user's body. Therefore, the user may train the orthosis as disclosed above for each separate profile. For example, after the user is finished training the orthosis for walking, the user can save the resulting thresholds under a walking profile, and retrain the orthosis for running. After retraining the orthosis for running, the user may save the resulting thresholds under a running profile, and train the orthosis for standing. It is understood that the aforementioned profiles are not intended to be limiting, and any number of profiles for any kind of human activity involving the legs can be programmed. It is further understood that as an alternative to training, the user can program the plurality of profiles by manually entering valgus/varus angle levels or actuation activation windows as disclosed above for each profile. The values that are manually entered or determined by the processor during training can be stored in the memory.

Figure 7:
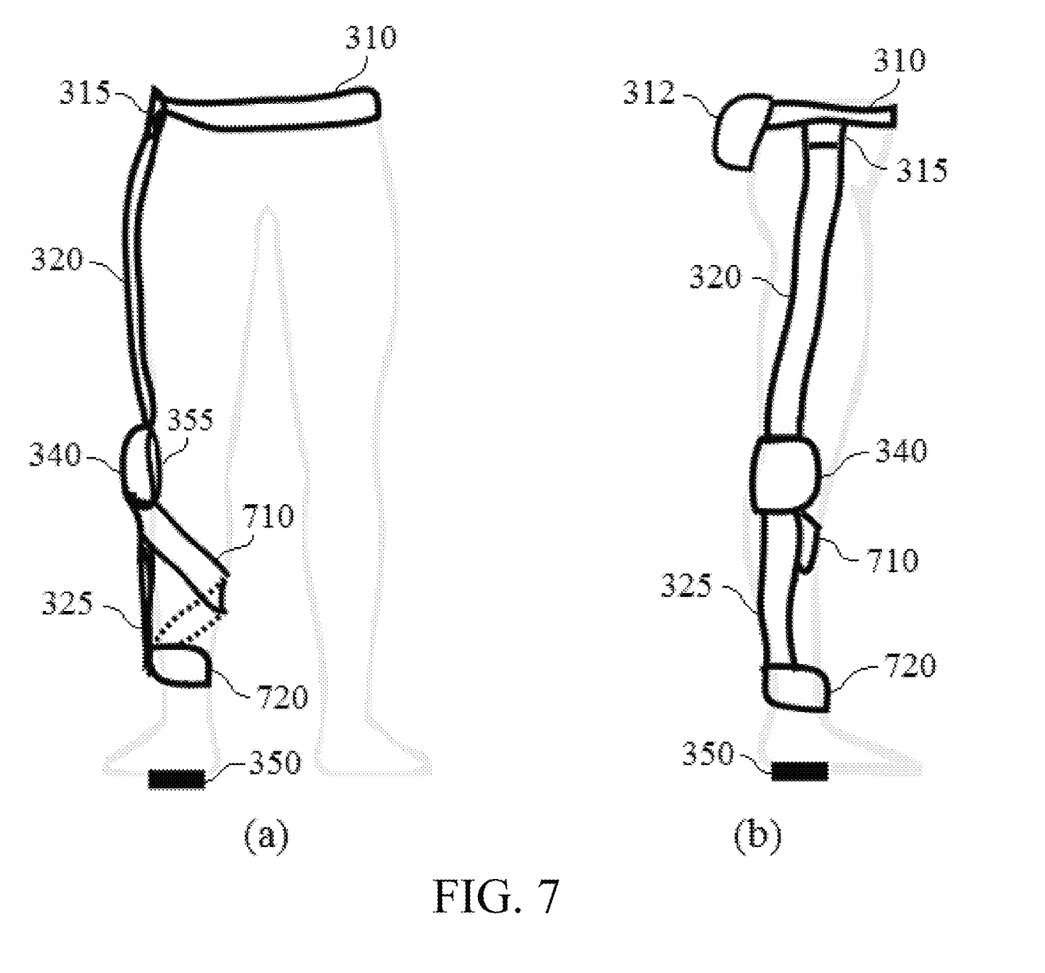
FIG. 7 depicts a frontal view and a lateral view of a robot-assisted orthosis with a calf strap in accordance with some embodiments.

FIG. 7 depicts a frontal view (a) and a lateral view (b) of a robot-assisted orthosis in accordance with another embodiment. For brevity, the items corresponding to those in FIG. 3 will not be described again here. When the robot-assisted orthosis disclosed in the embodiments above is not sufficient to produce the required stability or power, a cable wire system 710 can be used. In addition to, or as an alternative to, auxiliary parts 320 and 325, cable wire or any flexible material or combination thereof from waist belt 310 can extend along the thigh to an ankle region 720 (defined as being located under the calf region, or as part of the calf region). In this embodiment, actuator 340 adjusts valgus/varus levels by pulling and pushing (rolling up and down) the cable or flexible material, exerting lateral pressure on the knee.

Figure 8:
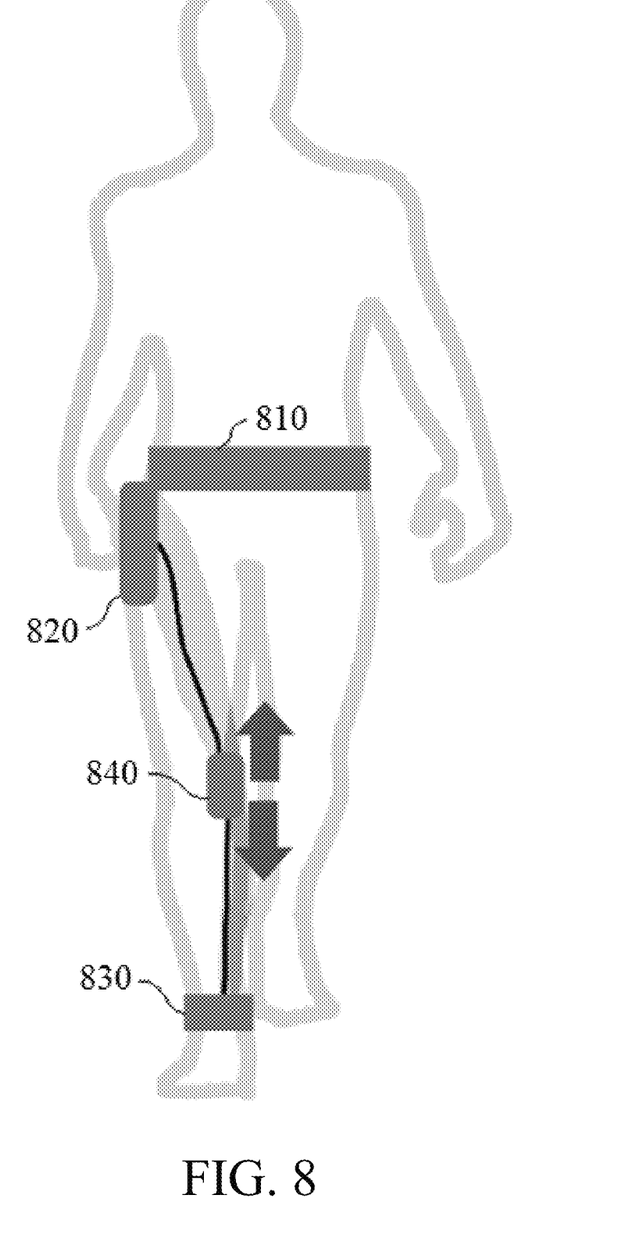
FIG. 8 depicts a frontal view of a robot-assisted orthosis with vertical movement in accordance with some embodiments.

FIG. 8 depicts a frontal view of a robot-assisted orthosis in accordance with another embodiment. Waist belt 810, auxiliary part 820, and ankle strap 830 all work together to support actuator 840, which can be positioned on the medial side of the knee, and can cause pressure on the knee in an upward or downward direction.

As used herein, the term "or" is intended to be interpreted as "or" or "and" unless explicitly stated otherwise. For example, "A or B" should be interpreted as "A only, B only, or both A and B" unless explicitly stated otherwise. Further, "A, B, or C" should be interpreted as "A only; B only; C only; A and B; B and C; A and C; or A, B, and C" unless explicitly stated otherwise.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

What is claimed is:

1. A knee orthosis apparatus for providing support to a user during a gait cycle, the apparatus comprising:
   a support structure adapted to be positioned at a lower extremity of the user;
   an actuator;
   a sensor configured to output a plurality of signals corresponding to detected leg movements; and
   a processor communicatively coupled to the sensor, wherein the processor is configured to:
   determine whether a knee of the user is in a stance phase or a swing phase of the gait cycle based on the plurality of signals,
   control the actuator to apply pressure on the support structure when the knee is in at least a portion of the stance phase, and
   control the actuator to release pressure on the support structure when the knee is in at least a portion of the swing phase.

2. The knee orthosis apparatus of claim 1, wherein the processor is configured to determine whether the knee is in the stance phase or the swing phase by comparing the plurality of signals to a threshold.

3. The knee orthosis apparatus of claim 2,
   wherein the sensor is an acceleration sensor and the plurality of signals represent a plurality of acceleration levels;
   wherein when a predetermined number of acceleration levels are lower than the threshold, the processor is configured to determine that the knee is in the stance phase; and wherein when a predetermined number of acceleration levels are higher than the threshold, the processor is configured to determine that the knee is in the swing phase.

4. The knee orthosis apparatus of claim 2,
wherein the sensor is an angular sensor and the plurality of signals represent a plurality of angular positions;
wherein the processor is further configured to calculate a rate of change of a predetermined number of angular positions;
wherein when the rate of change is lower than the threshold, the processor is configured to determine that the knee is in the stance phase; and
wherein when the rate of change is higher than the threshold, the processor is configured to determine that the knee is in the swing phase.

5. The knee orthosis apparatus of claim 2,
wherein the sensor is a force sensor and the plurality of signals represent a plurality of force levels;
wherein when a force level is higher than the threshold, the processor is configured to determine that the knee is in the stance phase; and
wherein when a force level is lower than the threshold, the processor is configured to determine that the knee is in the swing phase.

6. The knee orthosis apparatus of claim 2,
wherein the sensor is an electromyography (EMG) sensor or an electroencephalography (EEG) sensor and the plurality of signals represent EMG or EEG readings;
wherein when an EMG or EEG level is higher than the threshold, the processor is configured to determine that the knee is in the stance phase; and
wherein when an EMG or EEG level is lower than the threshold, the processor is configured to determine that the knee is in the swing phase.

7. The knee orthosis apparatus of claim 1, wherein the processor is further configured to vary an amount of pressure applied by the actuator during the stance phase according to a manually entered user input.

8. The knee orthosis apparatus of claim 7, wherein the processor is further configured to:
accept a plurality of user inputs corresponding to a plurality of variable actuation pressure levels;
store each user input in a separate profile in a memory; and
in response to receiving a profile selection from the user, control the actuator to apply a level of pressure corresponding to the selected profile.

9. The knee orthosis apparatus of claim 1, wherein the processor is further configured to vary a window of time during which the actuator applies pressure during the gait cycle, wherein the window starts proximate to a beginning of the stance phase, and ends proximate to an end of the stance phase according to a manually entered user input.

10. The knee orthosis apparatus of claim 9, wherein the processor is further configured to:
accept a plurality of user inputs corresponding with a plurality of actuation pressure windows;
store each user input in a separate profile in a memory; and
in response to receiving a profile selection from the user, control the actuator to apply pressure during a window corresponding to the selected profile.

11. The knee orthosis apparatus of claim 1, wherein:
the support structure comprises (i) an upper auxiliary support configured to be positioned at a thigh region of the lower extremity of the user and (ii) a lower auxiliary support configured to be positioned at a calf region of the user; and
the actuator is adapted to be positioned between the upper and lower auxiliary supports.

12. The knee orthosis apparatus of claim 1, wherein the sensor is configured to output the plurality of signals in accordance with leg movements during the gait cycle of the user.

13. The knee orthosis apparatus of claim 1, wherein controlling the actuator to apply pressure on the support structure comprises controlling the actuator to apply pressure in a lateral or medial direction with respect to a forward-facing direction of the user.

14. A method of providing support to a user during a gait cycle, the method comprising:
at a processor communicatively coupled to an actuator of a knee orthosis positioned proximate to a lower extremity of the user:
determining, based on signals from a sensor communicatively coupled to the processor, a current phase of the gait cycle of a knee of the user;
in accordance with a determination that the current phase is a stance phase, controlling the actuator to apply pressure on a support structure of the knee orthosis in a lateral or medial direction with respect to a forward-facing direction of the user; and
in accordance with a determination that the current phase is a swing phase, controlling the actuator to release pressure on the support structure of the knee orthosis.

15. The method of claim 14, wherein determining the current phase of the gait cycle of the user comprises comparing acceleration signals, angular position signals, force signals, electromyography (EMG) signals, and/or electroencephalography (EEG) signals from the sensor to a threshold.

16. The method of claim 14, further comprising: receiving one or more user inputs corresponding to variable actuation pressure levels; and wherein controlling the actuator to apply pressure comprises varying an amount of pressure in accordance with the received user inputs.

17. The method of claim 16, further comprising: storing each received user input in a separate profile in a memory; and in response to receiving a profile selection from the user, controlling the actuator to apply a level of pressure corresponding to the selected profile.

18. The method of claim 14, further comprising: varying, at the processor, a window of time during which the actuator applies pressure during the gait cycle, wherein the window starts proximate to a beginning of the stance phase, and ends proximate to an end of the stance phase.

19. The method of claim 18, further comprising: receiving user timing input for controlling timing of the window of time; and wherein the window of time starts and ends in accordance with the received user timing input.

20. The method of claim 18, further comprising: training, in a training mode of the processor, the knee orthosis to determine gait timing values by analyzing sensor readings over a plurality of gait cycles; and wherein the window of time starts and ends in accordance with the determined gait timing values.

* * * * *